(12) United States Patent
Fujimoto et al.

(10) Patent No.: US 7,728,162 B2
(45) Date of Patent: Jun. 1, 2010

(54) PROCESS FOR PREPARING PHOSPHORUS COMPOUNDS HAVING PHOSPHATE-PHOSPHONATE BOND

(75) Inventors: Kazuo Fujimoto, Tokyo (JP); Sakiko Tanaka, Aichi (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 320 days.

(21) Appl. No.: 11/718,296

(22) PCT Filed: Oct. 18, 2005

(86) PCT No.: PCT/JP2005/019132

§ 371 (c)(1),
(2), (4) Date: Apr. 30, 2007

(87) PCT Pub. No.: WO2006/049011

PCT Pub. Date: May 11, 2006

(65) Prior Publication Data

US 2009/0062554 A1    Mar. 5, 2009

(30) Foreign Application Priority Data

Nov. 2, 2004    (JP) .............................. 2004-319529

(51) Int. Cl.
*C07F 9/02* (2006.01)
(52) U.S. Cl. .............................. 558/73; 558/78; 558/79; 558/85; 558/86; 558/89; 558/117
(58) Field of Classification Search .................... 558/73, 558/78, 79, 85, 86, 89, 117
See application file for complete search history.

(56) References Cited

U.S. PATENT DOCUMENTS 4,697,030 A    9/1987    Hardy et al.

FOREIGN PATENT DOCUMENTS

| GB | 941706 | 11/1963 |
| JP | 49-126623 | 4/1974 |
| JP | 56-036512 | * 4/1981 |
| JP | 02-273688 | 11/1990 |
| JP | 11-100391 | 4/1999 |

OTHER PUBLICATIONS

E.N. Ofitserov et al.; Zhurnal Obshchei Khimii, 1982, vol. 52, No. 12, pp. 2704-2715.
C. Roch-Neirey et al.; Tetrahedron Letters, 2001, vol. 42, No. 4, pp. 643-645.
I.V. Konovalova et al.; Zhurnal Obshchei Khimii, 1979, vol. 49, No. 6, pp. 1424-1425.
English Language Abstract of JP 02-273688.
English Language Abstract of JP 11-100391.
Japanese Office Action for corresponding Japanese Patent Application No. JP 2006-543011, dated Feb. 19, 2009, and English language translation thereof.

* cited by examiner

*Primary Examiner*—Peter G O'Sullivan
(74) *Attorney, Agent, or Firm*—Greenblum & Bernstein, P.L.C.

(57) ABSTRACT

A novel process for preparing in a high purity and in a high yield phosphorus compounds having a phosphate-phosphonate bond within one molecule, along with only a small amount of a by-product, without being restricted by the kind of a phosphonate having an alcoholic hydroxyl group which is a raw material, without using a catalyst such as magnesium chloride, but only using a nitrogen-containing basic compound.

10 Claims, No Drawings

PROCESS FOR PREPARING PHOSPHORUS COMPOUNDS HAVING PHOSPHATE-PHOSPHONATE BOND

TECHNICAL FIELD

The present invention relates to a novel process for preparing in a high purity and in a high yield phosphorus compounds having a phosphate-phosphonate bond within one molecule which are useful as a flame-retarder for resins. According to the process of the present invention, the phosphorus compounds are prepared without being restricted by the kind of a phosphonate having an alcoholic hydroxyl group which is a raw material, without using a catalyst such as magnesium chloride, but only using a nitrogen-containing basic compound.

In the present invention, the term "phosphate-phosphonate bond" means a structure in which phosphorus atoms are bound together by a substituent consisting of an alkylene group and an oxygen atom, the alkylene group optionally containing a substituent.

BACKGROUND ART

Phosphorus compounds are used in various fields generally as a multifunctional compound, and various kinds of compounds have been developed. The phosphorus compounds have excellent functions especially as a flame-retarder, and have been widely used. Resins to which the phosphorus compounds are to give flame retardancy are diverse, and examples of such resins include thermoplastic resins such as polycarbonate, an ABS resin, polyphenylene ether (PPE) and polyester (e.g., polyethylene terephthalate, polybutylene terephthalate); and thermosetting resins such as polyurethane, an epoxy resin and a phenol resin. Also, these resins are in such diverse forms as molded article and fiber article.

Flame retardancy of a resin depends generally on the phosphorus content in a phosphorus compound. However, addition of the phosphorus compound in too large an amount to a resin in an attempt to give the resin a desired degree of flame retardancy could greatly deteriorate properties of the resin itself, especially mechanical properties thereof. Therefore, in order to give a resin sufficient flame retardancy by addition of the phosphorus compounds in a smaller amount, there has been a demand for phosphorus compounds having a higher phosphorus content.

Also, there has been the demand that the phosphorus compounds to be added have a high stability even at high temperatures because resins are to be exposed to significantly high temperatures at steps of kneading and molding.

Structures of phosphorus compounds are classified mainly as phosphate, phosphonate, phosphinate, phosphite, phosphonite, phosphinite, phosphine oxide, phosphine and the like. Every phosphorus compound has at least one of these structures within one molecule, and some have two or more different structures.

A phosphate-phosphonate is an exemplary structure, and known are a phosphate-phosphonate containing a halogen atom such as chlorine, bromine or the like within one molecule, a phosphate-phosphonate containing an alcoholic hydroxyl group within one molecule, and a phosphate-phosphonate containing a lower alkyl group such as ethyl group.

There are various processes known as a process for preparing such phosphate-phosphonates.

For example, the specification of U.S. Pat. No. 4,697,030 describes a process for synthesizing a phosphate-phosphonate by reacting a phosphonate having an alcoholic hydroxyl group with either phosphorus oxychloride or phosphorus chloridate in coexistence of Lewis acid such as magnesium chloride as a catalyst and triethylamine as a hydrogen chloride scavenger.

However, there is a problem in this process in that the kind of a phosphonate usable a raw material is restricted. In order words, when a phosphonate having a primary hydroxyl group is used as a raw material, the reaction proceeds without causing any problem, as described in the Examples of the above specification. However, when a phosphonate having a secondary or tertiary hydroxyl group is used as a raw material, there arises a problem that the reactivity with a compound having a pentavalent P(=O)—Cl (phosphorus-chlorine) bond is extremely lowed, resulting in a reduced yield of the target compound.

Also, even when a strongly basic catalyst such as 4-dimethylaminopyridine or 1,8-diazabicyclo(5,4,0)undecene-7 (DBU) is used in combination with triethylamine, the reactivity is not highly improved. Further, the above process, which uses the expensive catalysts, is not preferable in terms of cost. In addition, the use of these catalysts derives another problem of an increase in the amount of impurities prepared as a by-product.

Also, the specification of British Patent No. 941706 describes a process of synthesizing a trivalent phosphite compound with the use of, as raw materials, trialkyl phosphite, a carbonyl compound such as a ketone or an aldehyde, and phosphorus chloridate. The phosphate-phosphonate can be obtained by oxidizing the trivalent phosphite compound prepared by the above process.

However, phosphite compounds have a defect that they will readily decompose under an acidic atmosphere. The synthesis process in the above specification is a synthesis under an acidic atmosphere carried out by adding the carbonyl compound to the phosphorus chloridate without using any catalyst, and thus has a problem that the product will decompose to reduce the yield.

DISCLOSURE OF INVENTION

It is an object of the present invention to provide a novel process for preparing in a high purity and in a high yield phosphorus compounds having a phosphate-phosphonate bond within one molecule, along with only a small amount of a by-product, without being restricted by the kind of a phosphonate having an alcoholic hydroxyl group which is a raw material, without using a catalyst such as magnesium chloride, but only using a nitrogen-containing basic compound.

The present inventors, as a result of eager studies to solve the above problem, have found that, by using a phosphoro halidite (phosphorous halidite) having high reactivity as a raw material, a dehydrohalogenation reaction of a phosphonate having an alcoholic hydroxyl group and the phosphoro halidite can be carried out, and thereby a phosphate-phosphonate can be prepared in a high purity and in a high yield, along with only a small amount of a by-product, without being restricted by the kind of a phosphonate, without using a catalyst such as a magnesium chloride, but only using a nitrogen-containing basic compound, to complete the present invention.

Thus, the present invention provides a process for preparing a phosphorus compound, comprising the steps of:

subjecting a phosphonate having an alcoholic hydroxyl group, represented by the general formula (II):

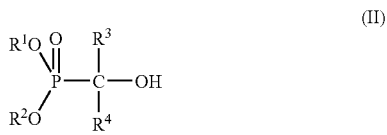

(II)

wherein $R^1$ and $R^2$ are, the same as or different from each other, a straight or branched alkyl, cycloalkyl or aryl group; or alternatively $R^1$ and $R^2$, together with the oxygen atom and phosphorus atom to which they are attached, may constitute a ring structure; $R^3$ and $R^4$ may be, the same as or different from each other, a hydrogen atom or a straight or branched alkyl or aryl group; or alternatively $R^3$ and $R^4$, together with the carbon atom to which they are attached, may constitute a ring structure and a phosphoro halidite represented by the general formula (III):

(III)

wherein $R^5$ and $R^6$ are, the same as or different from each other, a straight or branched alkyl, cycloalkyl or aryl group; or alternatively $R^5$ and $R^6$, together with the oxygen atom and phosphorus atom to which they are attached, may constitute a ring structure; and X is a halogen atom to a dehydrohalogenation reaction in the presence of a nitrogen-containing basic compound, to obtain a reaction product represented by the general formula (I'):

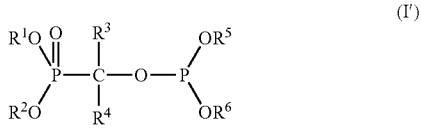

(I')

wherein $R^1$, $R^2$, $R^3$, $R^4$, $R^5$ and $R^6$ are as defined above; and then oxidizing the reaction product (I'), to thereby obtain a phosphorus compound having a phosphate-phosphonate bond, represented by the general formula (I):

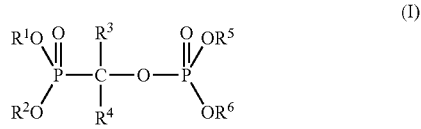

(I)

wherein $R^1$, $R^2$, $R^3$, $R^4$, $R^5$ and $R^6$ are as defined above.

According to the present invention, phosphorus compounds having a phosphate-phosphonate bond within one molecule can be prepared in a high purity and in high yields, along with only a small amount of a by-product, without being restricted by the kind of a phosphonate having an alcoholic hydroxyl group used as a raw material, without using a catalyst such as magnesium chloride, but only using a nitrogen-containing basic compound.

BEST MODE FOR CARRYING OUT THE INVENTION

The process for preparing phosphorus compound according to the present invention comprises subjecting a phosphonate (II) and a phosphoro halidite (III) to a dehydrohalogenation reaction in the presence of a nitrogen-containing basic compound, to obtain a reaction product (I'), and then oxidizing the reaction product (I'), to thereby obtain a phosphorus compound having a phosphate-phosphonate bond (I).

The nitrogen-containing basic compound serves as a hydrogen chloride scavenger.

$R^1$ and $R^2$ may be, the same as or different from each other, a straight or branched alkyl, cycloalkyl or aryl group. Or alternatively, $R^1$ and $R^2$, together with the oxygen atom and phosphorus atom to which they are attached, may constitute a ring structure.

Examples of the straight or branched alkyl groups for $R^1$ and $R^2$ include methyl, ethyl, n-propyl, iso-propyl, n-butyl, iso-butyl, sec-butyl, n-pentyl, n-hexyl, n-octyl and 2-ethylhexyl, among which particularly preferable are $C_2$-$C_8$ alkyl groups.

It is preferable that $R^1$ and $R^2$ are an alkyl group having 2 or more carbon atoms because in such a case, the phosphonate (II) is easy to hydrolyze, and a low yield of the phosphorus compound (I) may be resulted. Also, it is not preferable that at least one of $R^1$ and $R^2$ is an alkyl group having 9 or more carbon atoms, because an alcohol having a large number of carbon atoms that generates from the preparation of the phosphonate (II) may be left in the final product and difficult to remove.

Examples of the cycloalkyl groups for $R^1$ and $R^2$ include cyclopropyl, cyclobutyl, cyclopentyl, cyclohexyl, cycloheptyl, cyclooctyl, cyclononyl and cyclodecyl, among which particularly preferable are $C_5$-$C_7$ cycloalkyl groups and particularly preferable is a cyclohexyl group.

A cycloalkyl group having a ring structure constituted of 8 or more carbon atoms and a cycloalkyl group having a ring structure constituted of 4 or less carbon atoms are not preferable, because the cycloalkyl ring is prone to be unstable, and as a result, a compound resulting from cleavage of the ring may give adverse effects to the reaction system.

The cycloalkyl group for $R^1$ and $R^2$ may have a substituent. Examples of the substituents include $C_1$-$C_7$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the cycloalkyl groups having a substituent include a 3-methylcyclohexyl group and a 4-methylcyclohexyl group. It is preferable that the phosphonate (II) has such a group, because raw materials in synthesizing such a phosphonate (II) are readily available.

Examples of the aryl groups for $R^1$ and $R^2$ include phenyl, 1-naphtyl and 2-naphtyl.

The aryl group for $R^1$ and $R^2$ may have a substituent. Examples of the substituents include $C_1$-$C_9$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the aryl groups having a substituent include $C_6$-$C_{15}$ aryl groups such as 2-methylphenyl, 3-methylphenyl, 4-methylphenyl, 2,6-dimethylphenyl, 2,4-dimethylphenyl, 3,5-dimethylphenyl and 2,6-di-tert-butyl-4-methylphenyl.

It is preferable that the phosphonate (II) has a phenyl group, a 3-methylphenyl group or 4-methylphenyl group among the above aryl groups, because raw materials in synthesizing the phosphonate (II) are readily available.

Or alternatively, $R^1$ and $R^2$, together with the oxygen atom and phosphorus atom to which they are attached, may constitute a ring structure. The substituent $—R^1$-$R^2$— consisting of $R^1$ and $R^2$ in bond is preferably an alkylene group in which the sum of the numbers of carbon atoms contained in $R^1$ and $R^2$ is 2 to 9, and more preferably an alkylene group in which the sum is 2 to 6. The ring in the ring structure is preferably a five- to seven-membered ring, more preferably a five-membered ring or a six-membered ring, and particularly preferably a six-membered ring. Eight- and more-membered rings and four- and less-membered rings are not preferable, because these rings are prone to be unstable, and as a result, an acidic constituent [P—OH] produced due to cleavage of the ring may give adverse effects to the progress of the reaction.

Examples of the particularly preferable ring structures include a ring structure represented by the following general formula (VI):

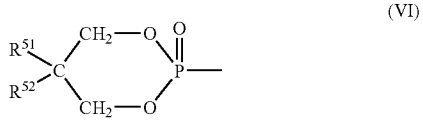

(VI)

wherein $R^{51}$ and $R^{52}$ are, the same as or different from each other, a hydrogen atom or a straight or branched alkyl group.

$R^{51}$ and $R^{52}$ are preferably such that the sum of the numbers of carbon atoms contained in $R^{51}$ and $R^{52}$ is 0 to 6. Specifically, a combination of a methyl group and a methyl group as $R^{51}$ and $R^{52}$, respectively, a combination of an ethyl group and an n-butyl group as $R^{51}$ and $R^{52}$, respectively, and the like combination.

$R^3$ and $R^4$ in the phosphonate (II) may be, the same as or different from each other, a hydrogen atom, or a straight or branched alkyl group or aryl group. Or alternatively $R^3$ and $R^4$, together with the carbon atom to which they are attached, may constitute a ring structure.

Examples of the straight or branched alkyl groups for $R^3$ and $R^4$ include methyl, ethyl, n-propyl, iso-propyl, n-butyl, iso-butyl, sec-butyl, n-pentyl and n-hexyl, among which particularly preferable are $C_1$-$C_6$ alkyl groups.

Examples of the aryl groups for $R^3$ and $R^4$ include phenyl, 1-naphtyl and 2-naphtyl.

The aryl group for $R^3$ and $R^4$ may have a substituent. Examples of the substituents include $C_1$-$C_5$ straight or branched alkyl groups such as methyl, ethyl, n-propyl, n-butyl, iso-butyl, sec-butyl, tert-butyl and n-pentyl.

Examples of the aryl groups having a substituent include phenyl groups having a methyl group, and naphtyl groups having a methyl group.

Or alternatively $R^3$ and $R^4$, together with the carbon atom to which they are attached, may constitute a ring structure represented by the following formula:

The substituent $—R^3$-$R^4$— consisting of $R^3$ and $R^4$ in bond is preferably an alkylene group in which the sum of the numbers of carbon atoms contained in $R^3$ and $R^4$ is 4 to 10. The ring in the ring structure is preferably a five- to seven-membered ring, more preferably a six-membered ring, and particularly preferably a six-membered ring having no substituent. Eight- and more-membered rings and four- and less-membered rings are not preferable, because these rings are prone to be unstable, and as a result, a compound produced due to cleavage of the ring may give adverse effects to the progress of the reaction.

The alkylene group may have a substituent. Examples of the substituents include $C_1$-$C_6$ straight or branched alkyl groups such as methyl, ethyl, n-propyl, n-butyl, iso-butyl, sec-butyl, tert-butyl and n-pentyl.

It is preferable that the sum of the numbers of carbon atoms contained in $R^3$ and $R^4$ is 1 to 12.

Also, it is preferable that the numbers of carbon atoms contained in $R^3$ and $R^4$ in the phosphonate (II) each are 1 or more and that the sum of the numbers of carbon atoms contained in $R^3$ and $R^4$ is 2 to 12.

If both of $R^3$ and $R^4$ are an alkyl group, and if the $R^3$ and $R^4$ together constitute a ring structure, the phosphonate (II) has a sterically bulky substituent, and as a result, it is expected that its reactivity with the phosphoro halidite (III) will be low. However, according to the preparation process of the present invention, the reaction proceeds smoothly contrary to the expectation.

It is preferable that a $R^3$ and $R^4$ combination in the phosphonate (II) is selected among (i) combinations of: a methyl group and a hydrogen atom; a methyl group and a methyl group; a methyl group and a ethyl group; a methyl group and an isobutyl group, a phenyl group and a hydrogen atom; a phenyl group and a methyl group; and a phenyl group and a phenyl group, and (ii) a substituent which, together with the carbon atom to which the substituent is attached to, constitutes a six-membered ring.

It is preferable that the phosphonate (II) is selected among: a compound represented by the formula (IV):

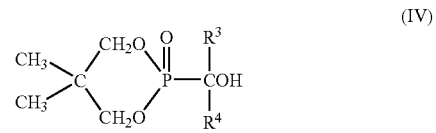

(IV)

wherein $R^3$ and $R^4$ are as defined above; a compound wherein both of $R^1$ and $R^2$ are an n-butyl group; and a compound wherein both of $R^1$ and $R^2$ are a 2-ethylhexyl group.

The phosphonate (II) can be synthesized by, for example, subjecting either an aldehyde or a ketone and a phosphite to an addition reaction (see, e.g., Japanese Unexamined Patent Publication No. Sho 49 (1974)-126623).

Examples of the phosphites used in the above addition reaction include dialkyl phosphites such as a diethyl phosphite, di-n-propyl phosphite, di-n-butyl phosphite, di-n-octyl phosphite and bis(2-ethylhexyl)phosphite; and cyclic phosphites such as neopentylene phosphite. Particularly preferable are dialkyl phosphites, each substituted with alkyl groups, and cyclic phosphites in terms of ease of acquisition as a raw material and in terms of cost.

Examples of the aldehydes include formaldehyde, acetaldehyde, propionaldehyde and benzaldehyde. Examples of the ketones include chain ketones such as acetone, methyl ethyl ketone and methyl iso-butyl ketone (MIBK); aromatic ketones such as acetophenone and benzophenone; and cyclic ketones such as cyclopentanone, cyclohexanone and methylcyclohexanone.

It is preferable to use a catalyst in the above addition reaction. Examples of the catalysts include basic catalysts such as alkaline metals, e.g., metallic sodium, metallic potassium, etc; alkaline-metal-containing bases, e.g., sodium hydroxide, sodium alkoxide, sodium amide, etc; aliphatic tertiary amines e.g., triethylamine, tributylamine, etc; aromatic amines e.g., pyridine, lutidine, picoline. Among these, preferable are the aliphatic tertiary amines. Also, these may be used in a combination of two or more.

Also, as a catalyst, a metallic halide such as magnesium chloride, aluminum chloride, zinc chloride, titanium tetrachloride or a boron trifluoride ether complex may be used. Also, these may be used in a combination of two or more.

In the above addition reaction, a combination of triethylamine, which is a basic catalyst, and magnesium chloride, which is a metallic halide, is preferable in terms of reactivity and ease of handling.

$R^5$ and $R^6$ in the phosphoro halidite (III) may be, the same as or different from each other, a straight or branched alkyl, cycloalkyl or aryl group. Or alternatively $R^5$ and $R^6$, together with the oxygen atom and phosphorus atom to which they are attached, may constitute a ring structure. X is a halogen atom.

Examples of the straight or branched alkyl groups for $R^5$ and $R^6$ include methyl, ethyl, n-propyl, iso-propyl, n-butyl, iso-butyl, sec-butyl, n-pentyl, n-hexyl, n-octyl and 2-ethylhexyl, among which particularly preferable are $C_2$-$C_8$ alkyl groups.

If at least one of $R^5$ and $R^6$ is a methyl group, the synthesis is difficult and as a result, the yield of the phosphorus compound (I) may decline. For this reason, it is preferable that $R^5$ and $R^6$ are an alkyl group having 2 or more carbon atoms. Also, it is not preferable that at least one of $R^5$ and $R^6$ is the an alkyl group having 9 or more carbon atoms, because in such a case, an alcohol having a large number of carbon atoms that generates from the preparation of the phosphoro halidite (III) may be left in the final product and difficult to remove.

Examples of the cycloalkyl groups for $R^5$ and $R^6$ include cyclopropyl, cyclobutyl, cyclopentyl, cyclohexyl, cycloheptyl, cyclooctyl, cyclononyl and cyclodecyl, among which preferable are $C_5$-$C_7$ cycloalkyl groups and particularly preferable are a cyclohexyl group.

A cycloalkyl group having a ring structure constituted of 8 or more carbon atoms and a cycloalkyl group having a ring structure constituted of 4 or less carbon atoms are not preferable, because the cycloalkyl ring is prone to be unstable, and as a result, a compound resulting from cleavage of the ring may give adverse effects to the reaction system.

The cycloalkyl group for $R^5$ and $R^6$ may have a substituent. Examples of the substituents include $C_1$-$C_7$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the cycloalkyl groups having a substituent include a 3-methylcyclohexyl group and a 4-methylcyclohexyl group. It is preferable that the phosphoro halidite (III) has such a group, because in such a case, the phosphoro halidite (III) is readily available as a raw material.

Examples of the aryl groups for $R^5$ and $R^6$ include phenyl, 1-naphtyl and 2-naphtyl.

The aryl group for $R^5$ and $R^6$ may have a substituent. Examples of the substituents include $C_1$-$C_9$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the aryl groups having a substituent include $C_6$-$C_{15}$ aryl groups such as 2-methylphenyl, 3-methylphenyl, 4-methylphenyl, 2,6-dimethylphenyl, 2,4-dimethylphenyl, 3,5-dimethylphenyl and 2,6-di-tert-butyl-4-methylphenyl.

It is preferable that the phosphoro halidite (III) has a phenyl group, a 3-methylphenyl group or 4-methylphenyl group among the above aryl groups, because such a phosphoro halidite (III) is readily available as a raw material.

Or alternatively, $R^5$ and $R^6$, together with the oxygen atom and phosphorus atom to which they are attached, may constitute a ring structure. The substituent —$R^5$-$R^6$— consisting of $R^5$ and $R^6$ in bond is preferably an alkylene group in which the sum of the numbers of carbon atoms contained in $R^5$ and $R^6$ is 2 to 9, and more preferably an alkylene group in which the sum is 2 to 6. The ring in the ring structure is preferably a five- to seven-membered ring, more preferably a five-membered ring or a six-membered ring, and particularly preferably a six-membered ring. Eight- and more-membered rings and four- and less-membered rings are not preferable, because these ring is prone to be unstable, and as a result, an acidic constituent [P—OH] produced due to cleavage of the ring may give adverse effects to progress of the reaction.

Particularly preferable examples of the ring structures include a ring structure represented by the following general formula (VII):

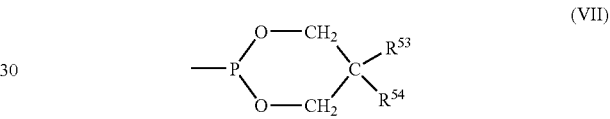

wherein $R^{53}$ and $R^{54}$ are, the same as or different from each other, a hydrogen atom, or a straight or branched alkyl group.

$R^{53}$ and $R^{54}$ are preferable such that the sum of the numbers of carbon atoms contained in $R^{53}$ and $R^{54}$ is 0 to 6. Specifically, a combination of a methyl group and a methyl group as $R^{53}$ and $R^{54}$, respectively, a combination of an ethyl group an n-butyl group as $R^{53}$ and $R^{54}$, respectively, and the like combination are mentioned.

Examples of the halogen atoms for X in the phosphoro halidite (III) include fluorine, chlorine, bromine and iodine. Chlorine and bromine are preferable, and chlorine is more preferable in terms of high reactivity.

The phosphoro halidite (III) is preferably the one represented by the formula (V):

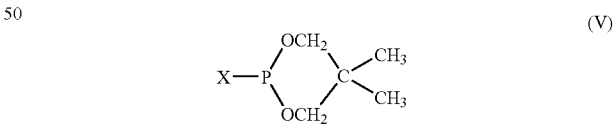

wherein X is a halogen atom.

The phosphoro halidite (III), for example, a cyclicalkylene phosphorus halidate, can be synthesized by the reaction of a phosphorus halide and a diol compound (see, e.g., Japanese Unexamined Patent Publication No. Hei 2 (1990)-273688).

Examples of the phosphorus halides used in the above reaction include phosphorus trichloride and phosphorus tribromide. Phosphorus trichloride is preferable in terms of ease of acquisition as a raw material and in terms of cost.

When a pentavalent phosphorus oxyhalide such as phosphorus oxychloride or phosphorus oxybromide is used as a raw material, an oxide of the phosphoro halidite (III) is obtained. The oxide is not preferable because of the extremely low reactivity with the phosphonate (II), which results in a failure to obtain in a high yield the phosphorus compound (I), which is the target of the present invention. One feature of the process for preparing phosphorus compounds according to the present invention is that after the reaction of the phosphonate (II) and the phosphoro halidite (III), the resulting reaction product is oxidized. Especially when the phosphoro halidite (III) has a ring structure, the difference in the yield of the phosphorus compound (I) is significant.

Also, examples of the diol compounds include 1,3-propanediol, 1,3-butanediol, 2,2-diethyl-1,3-propanediol, 2-ethyl-2-butyl-1,3-propanediol, neopentyl glycol and 2,2-diaryl-1,3-propanediol. 2-Ethyl-2-butyl-1,3-propanediol and neopentyl glycol are particularly preferable in terms of ease of acquisition as a raw material and in terms of cost.

It is preferable that, in the phosphonate (II), $R^1$ and $R^2$, together with the oxygen atom and phosphorus atom to which they are attached, constitute a ring structure and/or that, in the phosphoro halidite (III), $R^5$ and $R^6$, together with the oxygen atom and phosphorus atom to which they are attached, constitute a ring structure.

Next, there will be explained in detail the reaction of the phosphonate (II) and the phosphoro halidite (III) according to the present invention.

The preparation process of the present invention comprises the steps of subjecting a phosphonate (II) and a phosphoro halidite (III) to a dehydrohalogenation reaction in the presence of a nitrogen-containing basic compound (Step (1)), and then oxidizing the resulting reaction product (I'), to thereby obtaining a phosphorus compound (I) (Step (2)).

Examples of the nitrogen-containing basic compounds used in Step (1) include aliphatic tertiary amines such as triethylamine and tributylamine; and aromatic amines such as pyridine. Among these, preferable are aliphatic tertiary amines and particularly preferable is triethylamine.

The nitrogen-containing basic compound is used in about 1.0 to 1.2 moles with respect to 1 mole of the phosphoro halidite (III).

In Step (1), the phosphoro halidite (III) is preferably used in 1.0 to 1.5 moles, and more preferably in an amount of 1.01 to 1.2 moles, with respect to 1 mole of the phosphonate (II).

It is not preferable that the phosphoro halidite (III) is used in less than 1.0 mole with respect to 1 mole of the phosphonate (II), because in such a case, there will be left in the reaction product a large amount of unreacted phosphonate (II), and as a result, it may be difficult to remove the phosphonate (II) from the final product. Also, it is not preferable that the phosphoro halidite (III) is used in more than 1.5 mole with respect to 1 mole of the phosphonate (II), because in such a case, unreacted phosphoro halidite (III) may be left after completion of the reaction in Step (1) and form a loss of raw material though it can readily be removed by decomposition by washing.

The reaction temperature in Step (1) is preferably 10 to 100° C., and more preferably 20 to 70° C. It is not preferable that the reaction temperature is below 10° C. because the reactivity is lowered. Also, it is not preferable that the reaction temperature exceeds 100° C. because the nitrogen-containing basic compound may release or because the phosphoro halidite (III) may cause a secondary reaction.

Also, usually, about 1 to 5 hours is sufficient for the reaction time though the reaction time depends on conditions such as the reaction temperature.

The reaction in Step (1) may be carried out in the presence of an organic solvent as required.

The organic solvent is not particularly limited as long as it is a solvent inactive to the reaction. Examples of the organic solvents include hydrocarbon solvents such as hexane, cyclohexane, heptane, octane, benzene, toluene, xylene and a petroleum spirit; halogenated hydrocarbon solvents such as chloroform, carbontetrachloride, dichloromethane, dichloroethane, trichloroethane, tetrachloroethane, chlorobenzene and dichlorobenzene; and ether solvents such as diisopropyl ether, dibutyl ether, 1,4-dioxane and ethylene glycol diethyl ether. Among these, particularly referred are aromatic hydrocarbons such as toluene and chlorobenzene in terms of ease of handling.

If the reactions in preparing the phosphonate (II) and the phosphoro halidite (III) and the reaction in Step (1) are carried out sequentially as a continuous procedure, the same solvent is preferably used. This serves to reduce the number of solvent recovery steps.

After completion of the reaction in Step (1), an amine hydrohalide prepared as a by-product is preferably removed by, for example, a known method such as filtration or washing.

Next, in Step (2), the reaction product (I') obtained in Step (1) is oxidized by a known method, to obtain the phosphorus compound represented by the general formula (I). For example, the reaction product (I') and a hydrogen peroxide are reacted with each other under a basic condition (see, e.g., Japanese Unexamined Patent Publication No. Hei 11(1999)-100391).

In Step (2), if the reaction system is rendered acidic, the reaction product (I') decomposes, and therefore, it is necessary to always keep the reaction system basic.

For keeping the reaction system basic, a known basic compound can be used.

Examples of the basic compounds include alkaline metal hydroxides such as lithium hydroxide, sodium hydroxide, potassium hydroxide; carbonates such as sodium carbonate; ammonia; amines such as dimethylamine, trimethylamine, triethylamine, tributylamine and N,N-dimethylaniline; and aromatic complex ring bases such as pyridine and picoline. Among these, particularly preferable are sodium hydroxide and triethylamine. Also, these basic compounds may be used in a combination of two or more.

In Step (2), the hydrogen peroxide is preferably used in 1.0 to 1.5 moles, and more preferably in an amount of 1.01 to 1.2 moles with respect to 1 mole of the reaction product (I').

It is not preferable that the hydrogen peroxide is used in less than 1.0 mole with respect to 1 mole of the reaction product (I'), because the oxidation reaction will not be completed and a larger amount of unreacted reaction product (I') will be left in the reaction product, and as a result, the yield of the phosphorus compound (I) may decline. Also, it is not preferable in terms of safety that the hydrogen peroxide is used in too large an amount, because in such a case, oxidation reaction proceeds more sufficiently with increase in the amount of the hydrogen peroxide in use to raise the yield of the phosphorus compound (I), while unreacted hydrogen peroxide that incurs the risk of explosion will be left, and an extra step of reducing the hydrogen peroxide into water will become necessary. Therefore, it is appropriate to use the hydrogen peroxide in up to about 1.5 moles, and it is practical to use the hydrogen peroxide in up, to about 1.2 moles, with respect to 1 mole of the reaction product (I').

The reaction temperature in Step (2) is preferably 0 to 80° C., and more preferably 10 to 70° C. It is not preferable that the reaction temperature is below 0° C. because in such a case, the hydrogen peroxide that incurs the risk of explosion will accumulate in the reaction system to result in abrupt reaction.

Also, it is not preferable that the reaction temperature exceeds 80° C. because decomposition of the hydrogen peroxide itself will be accelerated.

Also, usually, about 1-5 hours is sufficient for the reaction time though the reaction time depends on conditions such as the reaction temperature.

The reaction in Step (2) may be carried out in the presence of an organic solvent as required.

The organic solvent is not particularly limited as long as it is a solvent inactive to the reaction. Organic solvents as mentioned in Step (1) may be used. In steps (1) and (2), the same solvent is preferably used to reduce the number of solvent recovery steps to 1.

From the reaction mixture thus obtained, the solvent and the low-boiling point components are removed under reduced pressure, to obtain a phosphorus compound (I) as the target compound.

Also, if it is intended to avoid impurities such as a nitrogen-containing basic compound and acidic components from being left in the reaction mixture, the impurities are preferably removed by a known method. Examples of the removal methods include acid washing, alkali washing, rinsing with water and vacuum distillation. However, if the amounts of impurities when the phosphorus compound (I) is added as a flame-retarder to a resin are small enough so as not to cause adverse effects to properties of polyurethane foam or molded articles such as an OA apparatus, purification as mentioned above is not particularly required. Thus, purification is employed as required.

With acid washing, the nitrogen-containing basic compound can be removed form the reaction mixture. Specifically, the reaction mixture is washed with acidic water such as hydrochloric acid, sulfuric acid, oxalic acid, nitric acid, phosphoric acid or citric acid.

With alkali washing, the acidic components and unreacted hydrogen peroxide can be removed from the reaction mixture through neutralization. Specifically, the reaction mixture obtained is washed with an alkaline aqueous solution such as sodium hydroxide, potassium hydroxide, calcium hydroxide or sodium carbonate.

In the above, the present invention has been explained by way of preferable examples. However, the present invention should not be construed as being limited to these examples. A skilled person in the art can carry out the present invention by applying equivalent ranges derived from the descriptions of preferable examples of the present application while referring to the descriptions of the present application and to common general technical knowledge. The disclosures of the documents cited in the present specification are incorporated by reference in its entirety, as is the case with the descriptions of the documents specifically contained therein.

EXAMPLES

The present invention will be explained in detail by way of the following examples and comparative examples, which should not be construed to limit the scope of the invention.

Example 1

Synthesis of Raw Material 1

Into a one-liter four-necked flask provided with a stirrer, a thermometer, a dropping device, a hydrochloric-acid-recovering device and a condenser, 112.3 g (1.08 moles) of neopentyl glycol and 123.5 g (110 wt % with respect to the neopentyl glycol) of toluene were fed. While stirring the resulting mixed solution at 20° C. in nitrogen atmosphere, 148.5 g (1.08 moles) of phosphorus trichloride was added thereto in 4 hours. Then, the mixed solution was stirred at the same temperature (20° C.) for 1 hour to raise the temperature finally up to 60° C., and a hydrogen chloride gas generated (75.6 g) was recovered. Thereafter, the pressure was gradually reduced to about 33 kPa, and the remaining hydrogen chloride gas was removed, thereby obtaining a solution containing neopentylenephosphorus chloridate (raw material 1) as a main component. The toluene, which was used as a solute, was not recovered here since it was to be used in the next step as well.

Synthesis of Raw Material 2

Next, into a two-liter four-necked flask provided with a stirrer, a thermometer, a dropping device, a hydrochloric-acid-recovering device and a condenser, 213.4 g (1.1 moles) of dibutyl phosphite, 5.6 g (0.06 moles) of triethylamine and 1.9 g (0.020 moles) of magnesium chloride were fed. While stirring the resulting mixed solution at 40° C., 70.2 g (1.2 moles) of acetone was added thereto in an hour. The mixed solution was further stirred for 1 hour at the same temperature (40° C.) to complete the reaction. Thereafter, the resulting reaction solution was washed with a 1% dilute hydrochloric acid aqueous solution and a saturated sodium carbonate aqueous solution successively and rinsed with water twice to remove the triethylamine and the magnesium chloride. Then, while heating the reaction mixture to 80° C., water was recovered under a reduced pressure of about 2.7 kPa. Further, nitrogen topping was carried out under the same conditions to remove the low-boiling point portions, thereby obtaining 254.6 g of dibutyl(1-hydroxy-1-methylethyl)phosphonate (raw material 2).

The purity of the product obtained was measured by gel permeation chromatography (GPC), and was found to be 99.0 area % (Table 2).

(Step (1))

After completion of the above reaction, 22.5 g of toluene and 114.3 g (1.13 moles) of triethylamine were fed into the two-liter four-necked flask containing the raw material 2, and the resulting mixed solution was stirred. Then, while maintaining the mixed solution at 60° C. in a thermostat, the mixed solution containing the raw material 1 was added from the dropping device (funnel) in 2 hours. Thereafter, the resulting reaction mixture was stirred at the same temperature (60° C.) for 1 hour to complete the reaction.

Water of 209.1 g (30 wt % with respect to the reaction mixture) was added to the reaction mixture. The resulting solution was stirred at the same temperature (60° C.) for 30 min. and then allowed to stand to be separated into phases. The aqueous phase was recovered to remove triethylamine, hydrochloride prepared as a by-product.

(Step (2))

Subsequently, the reaction solution obtained was cooled to 20° C., and 3.0 g (0.03 moles) of triethylamine was added thereto so that the mixed solution was of pH 10. Then, 104.9 g of a 35% hydrogen peroxide aqueous solution (1.08 moles as hydrogen peroxide) was added in 2 hours from the dropping device (funnel), while paying attention to heat generation in order for the temperature to go out of the range of 20 to 40° C. Thereafter, the mixture was stirred at 40° C. for 1 hour.

Then, the resulting reaction solution was heated to 60° C., washed with a 1% dilute hydrochloric acid aqueous solution and a saturated sodium carbonate aqueous solution successively and finally rinsed with water twice. Thereafter, while heating the reaction mixture to 100° C., water and toluene were recovered under a reduced pressure of 13.3 kPa. Further, steam topping and nitrogen topping were successively carried out at 100 to 110° C. under a reduced pressure of 2.7 kPa to remove the low-boiling point portions, thereby obtaining 390.3 g of a transparent and colorless liquid.

The purity of the product obtained was measured by gas chromatography (GC) under the conditions below, and was found to be 98.6 area % (Table 1).

GC Analysis Conditions
  Name of Device: GC-17A manufactured by SHIMADZU CORPORATION in Japan
  Column: DB-1 (manufactured by J&W Scientific Inc.) 0.25 mmφ×30 m, thickness 0.25 μm
  Detector: FID
  Carrier gas: He
  Temperature: INJ. 200° C.
  DET. 200° C.
  COL. 100° C.→(10° C./min.)→200° C.

Also, the yield was calculated according to GC and from the values of Table 2 and found to be 96.2% (Table 1).

The structure of the product obtained was determined according to IR, NMR, element analysis and absorption analysis based on P %.

IR (KBr):
2976, 1469, 1376, 1306, 1261, 1213, 1149, 1056, 1014, 915, 851, 813, 742, 624 cm$^{-1}$

NMR:
$^1$H-NMR (CDCl$_3$; 400 MHz); δ 4.26 (2H, d, $J_{HH}$=10 Hz, POCH$_2$C(CH$_3$)$_2$—), 4.144 (2H, t, $J_{HH}$=7 Hz, POCH$_2$CH$_2$CH$_2$CH$_3$), 4.141 (2H, t, $J_{HH}$=7 Hz, POCH$_2$CH$_2$CH$_2$CH$_3$), 3.86 (2H, dd, $J_{HH}$=10 Hz, $J_{PH}$=23 Hz, POCH$_2$C(CH$_3$)$_2$—), 1.80 (3H, s, PC(CH$_3$)$_2$O), 1.76 (3H, s, PC(CH$_3$)$_2$O), 1.69 (4H, m, POCH$_2$CH$_2$CH$_2$CH$_3$), 1.43 (4H, tq, $J_{HH}$=7 Hz, POCH$_2$CH$_2$CH$_2$CH$_3$), 1.29 (3H, s, POCH$_2$C(CH$_3$)$_2$—), 0.96 (6H, t, $J_{HH}$=7 Hz, POCH$_2$CH$_2$CH$_2$CH$_3$), 0.86 (3H, s, POCH$_2$C(CH$_3$)$_2$—) ppm $^{13}$C-NMR (CDCl$_3$; 100 MHz); δ 80.3 (dd, $^1J_{PC}$=179 Hz, $^2J_{PC}$=8 Hz, PC(CH$_3$)$_2$OP), 77.7 (d, $^2J_{PC}$=7 Hz, POCH$_2$C(CH$_3$)$_2$—), 66.5 (d, $^2J_{PC}$=7 Hz, POCH$_2$CH$_2$CH$_2$CH$_3$), 32.5 (d, $J_{PC}$=6 Hz), 31.9 (d, $^3J_{PC}$=5 Hz, POCH$_2$C(CH$_3$)$_2$—), 23.3, 21.7, 20.1, 18.6, 13.4 ppm element analysis and P % according to absorption analysis:
C: 47.9%, H: 8.5%, P: 15.5%

Example 2

Synthesis of Raw Material 1

The solution containing neopentylenephosphorus chloridate (raw material 1) as a main component was obtained in the same manner as in (synthesis of raw material 1) of Example 1.

Synthesis of Raw Material 3

Into a two-liter four-necked flask provided with a stirrer, a thermometer, dropping device, a hydrochloric-acid-recovering device and a condenser, 213.4 g (1.1 moles) of dibutylphosphite, 5.6 g (0.06 moles) of triethylamine and 1.05 g (0.011 moles) of magnesium chloride were fed. While stirring the resulting mixed solution at 25° C., 120.0 g (1.2 moles) of methyl isobutyl ketone (MIBK) was added thereto in 1 hour. The resulting mixed solution was further stirred for 1 hour at the same temperature (25° C.) to complete the reaction. Thereafter, the mixed solution was washed to remove the low-boiling point portions, as in (synthesis of raw material 2) of Example 1, and thus, the triethylamine and the magnesium chloride was removed from the mixed solution, to obtain 298.8 g of dibutyl(1-hydroxy-1,3-dimethylbutyl)phosphonate (raw material 3).

The purity of the product obtained was measured in the same manner as in Example 1, and was found to be 98.4 area % (Table 2).

(Step (1))
After completion of the above reaction, into the two-liter four-necked flask in which raw material 3 remained, 22.5 g of toluene and 114.3 g (1.13 moles) of triethylamine were fed, and the resulting mixed solution was stirred. Then, while maintaining the mixed solution at 25° C. in a thermostat, the mixed solution containing the raw material 1 was added from the dropping device (funnel) in 2 hours. Thereafter, the resulting reaction mixture was stirred at the same temperature (25° C.) for 1 hour to complete the reaction.

The reaction mixture was heated to 60° C., and 222.3 g (30 wt % with respect to the reaction mixture) of water was added to the reaction mixture. The resulting solution was stirred at the same temperature (60° C.) for 30 min. and then allowed to stand to be separated into phases. The aqueous phase was recovered to remove triethylamine hydrochloride prepared as a by-product.

(Step (2))
The reaction was carried out in the same manner as in (Step (2)) of Example 1, and thereby 433.0 g of a transparent and colorless liquid was obtained.

The purity of the product obtained was measured and the yield thereof was calculated in the same manner as in Example 1, and they were found to be 98.1 area % and 96.1%, respectively (Table 1).

The structure of the product obtained was determined according to IR, NMR, element analysis and absorption analysis based on P %.

IR (KBr):
2976, 1469, 1376, 1306, 1251, 1152, 1072, 992, 918, 899, 848, 806, 736, 624 cm$^{-1}$

NMR:
$^1$H-NMR (CDCl$_3$; 400 MHz); δ 4.41 (2H, d, $J_{HH}$=10 Hz, POCH$_2$C(CH$_3$)$_2$—), 4.15 (4H, m, POCH$_2$CH$_2$CH$_2$CH$_3$), 3.84 (2H, m, POCH$_2$C(CH$_3$)$_2$), 2.12 (1H, m, CH$_2$CH(CH$_3$)$_2$), 1.93 (2H, dd, $J_{HH}$=6 Hz, $^3J_{PH}$=14 Hz, POC(CH$_2$CH(CH$_3$)$_2$)—), 1.84 (3H, d, $^3J_{PH}$=16 Hz, POC(CH$_3$)(CH$_2$CH(CH$_3$)$_2$)P), 1.68 (4H, m, CH$_2$), 1.43 (4H, m, CH$_2$), 1.28 (3H, s, POCH$_2$C(CH$_3$)$_2$—), 1.07-0.92 (12H, m, CH$_3$), 0.86 (3H, s, POCH$_2$C(CH$_3$)$_2$—) ppm $^{13}$C-NMR (CDCl$_3$; 100 MHz); δ 83.9 (dd, $^1J_{PC}$=173 Hz, $^2J_{PC}$=8 Hz, PC(CH$_3$)(CH$_2$CH(CH$_3$)$_2$)OP), 77.9 (d, $^2J_{PC}$=7 Hz, POCH$_2$C(CH$_3$)$_2$—), 77.4 (d, $^2J_{PC}$=7 Hz, POCH$_2$C(CH$_3$)$_2$—), 66.7 (d, $^2J_{PC}$=7 Hz, POCH$_2$CH$_2$CH$_2$CH$_3$), 66.2 (d, $^2J_{PC}$=8 Hz, POCH$_2$CH$_2$CH$_2$CH$_3$), 45.9, 32.6 (d, $J_{PC}$=6 Hz), 32.5 (d, $J_{PC}$=6 Hz), 31.9 (d, $^3J_{PC}$=5 Hz, POCH$_2$C(CH$_3$)$_2$—), 24.5, 24.3, 23.9 (d, $J_{PC}$=6 Hz), 21.9, 21.7, 20.2, 18.7, 13.5 ppm element analysis and P % according to absorption analysis:
C: 51.5% H: 9.2%, P: 13.9%

Example 3

Synthesis of Raw Material 1

The solution containing neopentylenephosphorus chloridate (raw material 1) as a main component was obtained in the same manner as in (synthesis of raw material 1) of Example 1.

Synthesis of Raw Material 4

A synthesis was carried out in the same manner as in (synthesis of raw material 2) of Example 1 except that 117.6 g (1.2 moles) of cyclohexanone was used instead of acetone, 297.4 g of dibutyl (1-hydroxycyclohexyl)phosphonate (raw material 4) was obtained.

The purity of the product obtained was measured in the same manner as in Example 1, and was found to be 98.2 area % (Table 2).

(Step (1)) and (Step (2))

After completion of the above reaction, a reaction was carried out in the same manner as in Example 1 except that raw material 4 was used instead of raw material 2. Thereby, 432.8 g of a transparent and colorless liquid was obtained.

The purity of the product obtained was measured and the yield thereof was calculated in the same manner as in Example 1, and they were found to be 98.4 area % and 96.8%, respectively (Table 1).

The structure of the product obtained was determined according to IR, NMR, element analysis and absorption analysis based on P %.

IR (KBr):
2960, 1469, 1376, 1309, 1248, 1152, 1075, 1008, 922, 896, 883, 848, 816, 784, 726, 659, 618, 582 cm$^{-1}$

NMR:
$^1$H-NMR (CDCl$_3$; 400 MHz); δ 4.26 (2H, d, $J_{HH}$=10 Hz, POCH$_2$C(CH$_3$)$_2$—), 4.14 (2H, t, $J_{HH}$=7 Hz, POCH$_2$CH$_2$CH$_2$CH$_3$), 4.12 (2H, t, $J_{HH}$=7 Hz, POCH$_2$CH$_2$CH$_2$CH$_3$), 3.84 (2H, dd, $J_{HH}$=10 Hz, $J_{PH}$=23 Hz, POCH$_2$C(CH$_3$)$_2$—), 2.37 (2H, m, cyclo-CH$_2$), 1.91 (2H, m, cyclo-CH$_2$), 1.69 (10H, m, CH$_2$), 1.41 (4H, fq, $J_{HH}$=7 Hz, POCH$_2$CH$_2$CH$_2$CH$_3$), 1.28 (3H, s, POCH$_2$C(CH$_3$)$_2$—), 0.95 (6H, t, $J_{HH}$=7 Hz, POCH$_2$CH$_2$CH$_2$CH$_3$), 0.85 (3H, s, POCH$_2$C(CH$_3$)$_2$—) ppm $^{13}$C-NMR (CDCl$_3$; 100 MHz); δ 83.7 (dd, $^1J_{PC}$=171 Hz, $^2J_{PC}$=9 Hz, PCOP), 77.6 (d, $^2J_{PC}$=7 Hz, POCH$_2$C(CH$_3$)$_2$—), 66.5 (d, $^2J_{PC}$=7 Hz, POCH$_2$CH$_2$CH$_2$CH$_3$), 32.6 (d, $^3J_{PC}$=6 Hz, POCH$_2$CH$_2$CH$_2$CH$_3$), 31.9 (d, $^3J_{PC}$=6 Hz, POCH$_2$C(CH$_3$)$_2$—), 31.3 (d, m, cycloCH$_2$), 24.6, 22.0, 21.0, 20.9, 20.2, 18.7, 13.6 ppm element analysis and P % according to absorption analysis:
C: 51.8%, H: 8.8%, P: 14.0%

Example 4

Synthesis of Raw Material 1

The solution containing neopentylenephosphorus chloridate (raw material 1) as a main component was obtained in the same manner as in (synthesis of raw material 1) of Example 1.

Synthesis of Raw Material 2

The synthesis was carried out in the same manner as in (synthesis of raw material 2) of Example 1 except that 194.0 g (1.0 mole) of dibutyl phosphite, 5.1 g of (0.05 moles) of triethylamine, 1.7 g (0.018 moles) of magnesium chloride and 63.8 g (1.1 moles) of acetone were used and that washing and removal of the low-boiling point portions and thus triethylamine and magnesium chloride were not carried out. Thereby, 264.6 g of a solution containing dibutyl(1-hydroxy-1-methyl ethyl)phosphonate (raw material 2) was obtained as a main component.

(Step (1) and Step (2))

By carrying out a reaction in the same manner as in Example 1, 393.0 g of a transparent and colorless liquid was obtained.

The purity of the product obtained was measured and the yield thereof was calculated in the same manner as in Example 1, and they were found to be 96.8 area % and 95.1%, respectively (Table 1).

Also, the product was identified using the product obtained in Example 1.

Example 5

Synthesis of Raw Material 1

The solution containing neopentylenephosphorus chloridate (raw material 1) as a main component was obtained in the same manner as in (synthesis of raw material 1) of Example 1.

Synthesis of Raw Material 5

A solution of 247.6 g containing dibutyl(1-hydroxyethyl) phosphonate (raw material 5) was obtained as a main component in the same manner as in (synthesis of raw material 2) of Example 1 except that 194.0 g (1.0 mole) of dibutyl phosphite, 5.1 g (0.05 moles) of triethylamine and 0.14 g (0.0015 moles) of magnesium chloride were used; that 48.4 g (1.1 moles) of acetaldehyde was used instead of acetone; and that washing and removal of the low-boiling point portions were not carried out and thus triethylamine and magnesium chloride were not removed.

(Step (1) and Step (2))

By carrying out a reaction in the same manner as in Example 1 except that the raw material 5 was used instead of the raw material 2, 381.8 g of a transparent and colorless liquid was obtained.

The purity of the product obtained was measured and the yield thereof was calculated in the same manner as in Example 1, and they were found to be 96.1 area % and 95.1%, respectively (Table 1).

The structure of the product obtained was determined according to IR, NMR, element analysis and absorption analysis based on P %.

IR (KBr):
2976, 1469, 1376, 1302, 1248, 1120, 1056, 1014, 918, 854, 838, 742, 624 cm$^{-1}$

NMR:
$^1$H-NMR (CDCl$_3$; 400 MHz); δ 4.56 (1H, m, POCH(CH$_3$)P), 4.26 (2H, d, $J_{HH}$=10 Hz, POCH$_2$C(CH$_3$)$_2$—), 4.14 (2H, t, $J_{HH}$=7 Hz, POCH$_2$CH$_2$CH$_2$CH$_3$), 4.12 (2H, t, $J_{HH}$=7 Hz, POCH$_2$CH$_2$CH$_2$CH$_3$), 3.86 (2H, dd, $J_{HH}$=10 Hz, $J_{PH}$=23 Hz, POCH$_2$C(CH$_3$)$_2$—), 1.98 (3H, d, $J_{HH}$=7 Hz, POCH(CH$_3$)P), 1.43 (4H, tq, $J_{HH}$=7 Hz, POCH$_2$CH$_2$CH$_2$CH$_3$), 1.29 (3H, s, POCH$_2$C(CH$_3$)$_2$—), 0.98 (6H, t, $J_{HH}$=7 Hz, POCH$_2$CH$_2$CH$_2$CH$_3$), 0.86 (3H, s, POCH$_2$C(CH$_3$)$_2$—) ppm $^{13}$C-NMR (CDCl$_3$; 100 MHz); δ 79.4 (dd, $^1J_{PC}$=180 Hz, $^2J_{PC}$=8 Hz, PCH(CH$_3$)OP), 77.7 (d, $^2J_{PC}$=7 Hz, POCH$_2$C(CH$_3$)$_2$—), 66.5 (d, $^2J_{PC}$=7 Hz, POCH$_2$CH$_2$CH$_2$CH$_3$), 32.5 (d, $^3J_{PH}$=6 Hz, POCH$_2$CH$_2$CH$_2$CH$_3$), 31.9 (d, $^3J_{PH}$=5 Hz, POCH$_2$C(CH$_3$)$_2$—), 23.3, 21.7, 20.1, 13.4 ppm element analysis and P % according to absorption analysis:
C: 46.6%, H: 7.8%, P: 16.1%

Comparative Example

Synthesis of Raw Material 6

Into a one-liter four-necked flask provided with a stirrer, a thermometer, dropping device, a hydrochloric-acid-recovering device and a condenser, 117.5 g (1.13 moles) of neopentyl glycol and 129.3 g (110 wt % with respect to the neopentyl glycol) of toluene were fed. While stirring the resulting mixed solution at 50° C., 171.9 g (1.12 moles) of phosphorus oxychloride was added in an hour. After completion of the addition, the mixture was heated to 75° C. in an hour to be reacted to recover a hydrogen chloride gas (70.9 g) generated. Thereafter, the pressure was gradually reduced to about 33 kPa and the remaining hydrogen chloride gas was removed, thereby obtaining a solution containing neopentylenephosphorus chloridate (raw material 6) as a main component. The toluene, which was used as a solute, was not recovered here since it was to be used in the next step as well.

Synthesis of Raw Material 2

The solution containing dibutyl(1-hydroxy-1-methylethyl)phosphonate (raw material 2) as a main component was obtained in the same manner as in (synthesis of raw material 2) of Example 4.

After completion of the above reaction, the solution containing the raw material 2 as a main component and 3.2 g (0.03 moles) of magnesium chloride were added to the solution containing the raw material 6 as a main component, and the resulting mixture was stirred. Then, while maintaining the mixed solution at 50° C. in a thermostat, 113.1 g (1.12 moles) of triethylamine was added from the dropping device (funnel) in 2 hours. Thereafter, the reaction mixture was stirred at the same temperature (50° C.) for 12 hours.

Subsequently, a 2.5% dilute hydrochloric acid aqueous solution was added, and the resulting mixture was stirred so that excess triethylamine was neutralized to produce a hydrochloride from the mixture. And the hydrochloride was then removed. Further the mixture was washed to remove the remaining hydrochloride. Next, neopentylenepyrophosphate prepared as a by-product was decomposed with a saturated sodium carbonate aqueous solution, and further the mixture was washed twice to remove impurities. Thereafter, while heating the resulting reaction mixture to 100° C., water and toluene were recovered under a reduced pressure of 13.3 kPa. Further, steam topping and nitrogen topping were successively carried out at 100 to 110° C. under a reduced pressure of 2.7 kPa to remove the low-boiling point portions, thereby obtaining 275.3 g of a transparent and colorless liquid.

The purity of the product obtained was measured and the yield thereof was calculated in the same manner as in Example 1, and they were found to be 86.8 area % and 59.7%, respectively (Table 1).

Also, the product was identified using the product obtained in Example 1.

Comparative Example 2

Synthesis of Raw Material 6

The solution containing neopentylenephosphorus chloridate (raw material 6) as a main component was obtained in the same manner as in (synthesis of raw material 6) of Comparative Example 1.

Synthesis of Raw Material 5

The solution containing dibutyl(1-hydroxyethyl)phosphonate (raw material 5) as a main component was obtained in the same manner as in (synthesis of raw material 5) of Example 5.

After completion of the above reaction, the solution containing the raw material 5 as a main component and 1.2 g (0.013 moles) of magnesium chloride were added to the solution containing the raw material 6 as a main component, and the resulting mixed solution was stirred. Then, while maintaining the mixed solution at 40° C. in a thermostat, 113.1 g (1.12 moles) of triethylamine was added from the dropping device (funnel) in 2 hours. Thereafter, the reaction mixture was stirred at the same temperature (40° C.) for four hour.

Subsequently, a 1.0% dilute hydrochloric acid aqueous solution was added to the mixture, and the resulting mixture was stirred to neutralize excess triethylamine and thus to produce a hydrochloride therefrom, which was then removed. Further the mixture was washed to remove the remaining hydrochloride. Next, neopentylenepyrophosphate prepared as a by-product was decomposed with a saturated sodium carbonate aqueous solution, and further the mixture was washed twice to remove impurities. Thereafter, while heating the resulting reaction mixture to 100° C., and water and toluene were recovered under a reduced pressure of 13.3 kPa. Further, steam topping and nitrogen topping were successively carried out at 100 to 100° C. under a reduced pressure of 2.7 kPa to remove the low-boiling point portions, thereby obtaining 342.4 g of a transparent and pale brownish liquid.

The purity of the product obtained was measured and the yield thereof was calculated in the same manner as in Example 1, and they were found to be 96.6 area % and 85.7%, respectively (Table 1).

Also, the product was identified using the product obtained in Example 5.

Comparative Example 3

The process of Comparative Example 2 was followed except that the raw material 5 was used after the raw material 5 was purified by washing and by removing the low-boiling point portions thereby removing triethylamine and magnesium chloride; and that magnesium chloride was not used during the reaction between a solution containing the raw material 5 purified as a main component and the solution containing the raw material 6 as a main component.

However, when the solution after completion of the reaction was analyzed by GC, it was found that only neopentylenepyrophosphate was prepared as a by-product and that no reaction proceeded.

Comparative Example 4

Similar to the Reaction Described in Example 57 of the Specification of British Patent No. 941706

Into a one-liter four-necked flask provided with a stirrer, a thermometer, dropping device, and a condenser, 250.0 g (1.0 mole) of tributyl phosphite (manufactured by TOKYO KASEI KOGYO CO., LTD in Japan) and 168.5 g (1.0 mole) of neopentylenephosphorus chloridate obtained by purifying the solution containing the raw material 1 as a main component were fed, and the resulting mixture was stirred. Then, while maintaining the mixed solution at 10° C. in a thermostat, 58.0 g (1.0 mole) of acetone was added thereto from the dropping device (funnel) in an hour.

The reaction mixture was heated to 70° C. after completion of the addition, and then maintained at the same temperature (70° C.) for 1 hour. When the reaction mixture was analyzed by GC, it was found that no target compound was prepared, and it was judged that no target compound can be obtained.

Comparative Example 5

A Modified Reaction Process Similar to the One Described in Example 57 of the Specification of British Patent No. 941706

Into a one-liter four-necked flask provided with a stirrer, a thermometer, dropping device, and a condenser, 250.0 g (1.0 mole) of tributylphosphite (manufactured by TOKYO KASEI KOGYO CO., LTD in Japan) and 168.5 g (1.0 mole) of neopentylenephosphorus chloridate obtained by purifying the solution containing the raw material 1 as a main component were fed, and the resulting mixture was stirred. Then, while maintaining the mixed solution at 10° C. in a thermostat, a mixed solution of 58.0 g (1.0 mole) of acetone and 101.0 g (1.0 mole) of triethylamine were added from the dropping device (funnel) in an hour.

The reaction mixture was heated to 70° C. after completion of the addition, and then maintained at the same temperature (70° C.) for 1 hour. When the reaction mixture was analyzed by GC, it was found that about 10% of uncertain component was prepared and that the most was left as raw material, and it was judged that the target compound cannot be obtained.

TABLE 1

| | Example | | | | | Comparative Example | | |
|---|---|---|---|---|---|---|---|---|
| | 1 | 2 | 3 | 4 | 5 | 1 | 2 | 3-5 |
| Purity (%) | 98.6 | 98.1 | 98.4 | 96.8 | 96.1 | 86.8 | 96.6 | No reaction |
| Yield (%) | 96.2 | 96.1 | 96.8 | 95.1 | 95.1 | 59.7 | 85.7 | — |

The values in Table 2 were calculated on the following assumptions:

Assumption 1: The raw material 1 of 1.08 moles was present in a solution containing the raw material 1 as a main component.

Assumption 2: The raw material 6 of 1.12 moles was present in a solution containing the raw material 6 as a main component.

Assumption 3: In Example 4 and Comparative Example 1, 1.00 mole of the raw material 2 was present in a solution containing the raw material 2 as a main component.

Assumption 4: In Example 5 and Comparative Example 2, 1.00 mole of the raw material 5 was present in a solution containing the raw material 5 as a main component.

Assumption 5: Area % obtained according to GPC analysis and GC analysis of each component was regarded as being equal to wt %.

Assumption 6: The oxidation reaction ratio in Step (2) was regarded as 100%.

From the results in Table 1, it is understood that, by subjecting the phosphonate having an alcoholic hydroxyl group and the phosphoro halidite to a dehydrohalogenation reaction in the presence of the nitrogen-containing basic compound and by oxidizing the obtained reaction product, a phosphate-phosphonate can be synthesized in a high purity and in a high yield without the use of a catalyst such as a magnesium chloride (Examples 1 to 5).

Especially it is understood that even when a tertiary alcohol with low reactivity (Example 1) or a tertiary alcohol with steric hindrance whose reactivity is expected to be low (Examples 2 and 3) is used as a raw material, a phosphate-phosphonate having high reactivity can be synthesized in a high purity and in a high yield.

Also, even when an unpurified raw material is used in the reaction in Step (1), it is understood that a phosphate-phosphonate can be synthesized in a high purity and in a high yield (Examples 4 and 5).

TABLE 2

| | Step (1) | | | | | | Step (2) Final target | | | | |
|---|---|---|---|---|---|---|---|---|---|---|---|
| | Raw material | | | | | | | | Actual | | |
| | Raw material | | A | B GPC | Actual weight A × B | | Amount obtained C | D GC | actual amount obtained C × D | Theoretical amount obtained | Yield |
| | | mol | g | % | g | mol | g | % | g | g | % |
| Example 1 | Raw material 1 | 1.08 | Raw material 2 | 254.6 | 99.0 | 252.1 | 1.00 | 390.3 | 98.6 | 384.8 | 400.0 | 96.2 |
| Example 2 | Raw material 1 | 1.08 | Raw material 3 | 298.8 | 98.4 | 294.0 | 1.00 | 433.0 | 98.1 | 424.8 | 442.0 | 96.1 |
| Example 3 | Raw material 1 | 1.08 | Raw material 4 | 297.4 | 98.2 | 292.0 | 1.00 | 432.8 | 98.4 | 425.9 | 440.0 | 96.8 |
| Example 4 | Raw material 1 | 1.08 | Raw material 2 | — | — | — | 1.00 | 393.0 | 96.8 | 380.4 | 400.0 | 95.1 |
| Example 5 | Raw material 1 | 1.08 | Raw material 5 | — | — | — | 1.00 | 381.8 | 96.1 | 366.9 | 386.0 | 95.1 |
| Comparative Example 1 | Raw material 6 | 1.12 | Raw material 2 | — | — | — | 1.00 | 275.3 | 86.8 | 239.0 | 400.0 | 59.7 |
| Comparative Example 2 | Raw material 6 | 1.12 | Raw material 5 | — | — | — | 1.00 | 342.4 | 96.6 | 330.8 | 386.0 | 85.7 |

Further, even when a primary alcohol such as dibutyl(hydroxymethyl)phosphonate is used as a raw material, the same effects as mentioned above can be obtained.

On the other hand, where a pentavalent phosphorus compound is used as a raw material instead of a trivalent phosphorus compound (phosphoro halidite)(Comparative Examples 1 and 2), there are advantages that no oxidation reaction is required and that the number of reaction steps is reduced. However, the purity and the yield are inferior to those in Examples 1-5.

In Comparative Examples 1 and 2, neopentylenepyrophosphate represented by the formula below was prepared as a by-product.

This compound cannot be removed from the target compound by steam topping or nitrogen topping, but can be removed only by hydrolysis using alkali. However, hydrolysis also serves to decompose the target compound to some extent, resulting in a reduced yield.

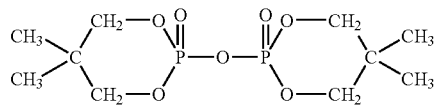

Where the pentavalent phosphorus compound was used instead of the trivalent phosphorus compound while only the triethylamine was used as the nitrogen-containing basic compound and no magnesium chloride was used as the catalyst (Comparative Example 3), the reaction did not proceed at all.

From this, it is understood that where the pentavalent phosphorus compound is used as the raw material, magnesium chloride needs to be used as a catalyst, and also as in Comparative Examples 1 and 2, a by-product is generated to result in a reduced yield.

The synthesis process described in the specification of British Patent No. 941706 and its modified processes (Comparative Examples 4 and 5) are ones efficient in that they can unify the step of synthesizing phosphonate having an alcoholic hydroxyl group that serves as a raw material and Step (1) into one step and in that they require no catalyst. However, Comparative Examples 4 and 5 provided no target compound.

In Comparative Example 4, in which the reaction was carried out in a strong acid atmosphere, it is assumed that the target compound, if generated, may have decomposed immediately. For this reason, in Comparative Example 5, the triethylamine was used to render the reaction atmosphere basic and thereby to block the target compound from decomposing. However, as in Comparative Example 4, obtained was only the uncertain component, and the target compound was not obtained.

This application is related to Japanese application No. 2004-319529 filed on Nov. 2, 2004, whose priority is claimed and the disclosure of which is incorporated by reference in its entirety.

The invention claimed is:

1. A process for preparing a phosphorus compound, comprising:
subjecting a phosphonate having an alcoholic hydroxyl group, represented by the general formula (II):

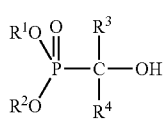

wherein $R^1$ and $R^2$ are, the same as or different from each other, a straight or branched alkyl, cycloalkyl or aryl group; or alternatively $R^1$ and $R^2$, together with the oxygen atom and phosphorus atom to which they are attached, may constitute a ring structure; $R^3$ and $R^4$ may be, the same as or different from each other, a straight or branched alkyl or aryl group; or alternatively $R^3$ and $R^4$, together with the carbon atom to which they are attached, may constitute a ring structure and
a phosphoro halidite represented by the general formula (III):

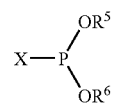

wherein $R^5$ and $R^6$ are, the same as or different from each other, a straight or branched alkyl group, and together with the oxygen atom and phosphorus atom to which they are attached, may constitute a ring structure; and X is a halogen atom
to a dehydrohalogenation reaction in the presence of a nitrogen-containing basic compound, to obtain a reaction product represented by the general formula (I'):

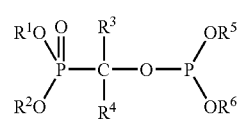

wherein $R^1$, $R^2$, $R^3$, $R^4$, $R^5$ and $R^6$ are as defined above; and then
oxidizing the reaction product (I'), to thereby obtain a phosphorus compound having a phosphate-phosphonate bond, represented by the general formula (I):

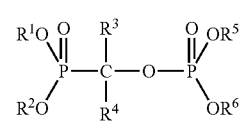

wherein $R^1$, $R^2$, $R^3$, $R^4$, $R^5$ and $R^6$ are as defined above.

2. The process for preparing a phosphorus compound of claim 1, wherein the nitrogen-containing basic compound is an aliphatic tertiary amine.

3. The process for preparing a phosphorus compound of claim 2, wherein the aliphatic tertiary amine is triethylamine.

4. The process for preparing a phosphorus compound of claim 1, wherein $R^1$ and $R^2$ in the phosphonate (II) together constitute a ring structure.

5. The process for preparing a phosphorus compound of claim 4, wherein the phosphonate (II) is selected among:

a compound represented by the formula (IV):

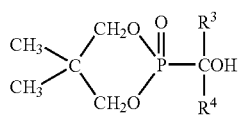

(IV)

wherein $R^3$ and $R^4$ are as defined above;

a compound wherein both of $R^1$ and $R^2$ are an n-butyl group; and a compound wherein both of $R^1$ and $R^2$ are a 2-ethylhexyl group.

6. The process for preparing a phosphorus compound of claim 4, wherein the phosphoro halidite (III) is represented by the formula (V):

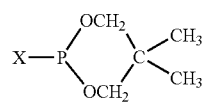

(V)

wherein X is a halogen atom.

7. The process for preparing a phosphorus compound of claim 1, wherein the numbers of carbon atoms contained in $R^3$ and $R^4$ in the phosphonate (II) each are one or more, and the sum of the numbers of carbon atoms contained in $R^3$ and $R^4$ is 2 to 12.

8. The process for preparing a phosphorus compound of claim 1, wherein a $R^3$ and $R^4$ combination in the phosphonate (II) is selected among (i) combinations: of a methyl group and a methyl group; a methyl group and a ethyl group; a methyl group and an isobutyl group; a phenyl group and a methyl group; and a phenyl group and a phenyl group, and (ii) a substituent which, together with the carbon atom to which the substituent is attached to, constitutes a six-membered ring.

9. The process for preparing a phosphorus compound of claim 1, wherein the nitrogen-containing basic compound is used in an amount of 1.0 to 1.2 moles with respect to one mole of the phosphoro halidite (III).

10. The process for preparing a phosphorus compound of claim 1, wherein 1.0 to 1.5 moles of hydrogen peroxide is used with respect to one mole of the reaction product (I') for the oxidation of the reaction product (I').

* * * * *